United States Patent [19]

Beverly

[11] Patent Number: 5,163,924
[45] Date of Patent: Nov. 17, 1992

[54] IMPLANTABLE BONE DRAIN

[76] Inventor: Michael Beverly, 30 Sheen Road, Richmond, Surrey, TW9 1AW, United Kingdom

[21] Appl. No.: 496,184
[22] PCT Filed: Aug. 25, 1987
[86] PCT No.: PCT/GB87/05999
 § 371 Date: Apr. 14, 1989
 § 102(e) Date: Apr. 14, 1989
[87] PCT Pub. No.: WO88/00599
 PCT Pub. Date: Mar. 10, 1988

Related U.S. Application Data

[63] Continuation of Ser. No. 318,924, Feb. 23, 1989, abandoned.

[30] Foreign Application Priority Data

Aug. 26, 1986 [GB] United Kingdom ............. 8620650

[51] Int. Cl.$^5$ ............................................. A61M 27/00
[52] U.S. Cl. ................................. 604/264; 604/280; 604/8; 604/266; 604/93
[58] Field of Search ............. 604/164, 158, 280, 282, 604/266, 93, 175, 8-10, 264

[56] References Cited

U.S. PATENT DOCUMENTS

| | | |
|---|---|---|
| 3,626,950 | 12/1971 | Schulte . |
| 3,750,667 | 8/1973 | Pshenichny et al. ............ 604/164 X |
| 3,938,529 | 2/1976 | Gibbons ............................. 604/282 |
| 4,142,517 | 3/1979 | Stavropoulos et al. ........ 606/179 X |
| 4,160,454 | 7/1979 | Foux . |
| 4,317,452 | 3/1982 | Russo ................................. 604/282 |
| 4,391,276 | 7/1983 | Lazarus et al. ..................... 604/266 |
| 4,398,910 | 8/1983 | Blake et al. ............................ 604/93 |
| 4,579,555 | 1/1986 | Russo .................................. 604/282 |
| 4,645,493 | 2/1987 | Ferrando et al. .................. 604/280 |
| 4,696,308 | 9/1987 | Meller et al. ....................... 128/754 |
| 4,755,171 | 7/1988 | Tennant ............................. 604/280 |

FOREIGN PATENT DOCUMENTS

| | | |
|---|---|---|
| 88138A | 2/1896 | Fed. Rep. of Germany . |
| 8602133 | 4/1986 | Fed. Rep. of Germany . |
| 2240026 | 3/1975 | France . |
| 189127A | 5/1923 | United Kingdom . |
| 2130890A | 6/1984 | United Kingdom . |

OTHER PUBLICATIONS

Patent Cooperation Treaty Int. Prelim. Exam. Report
International Search Report.

Primary Examiner—Robert A. Hafer
Assistant Examiner—Kerry Owens
Attorney, Agent, or Firm—Kane, Dalsimer, Sullivan, Kurucz, Levy, Eisele and Richard

[57] ABSTRACT

An implantable bone drain for relieving intraosseous pressure is formed of a bio-compatible material and has an outer surface shaped to prevent or limit movement of the drain out of position after implantation and there may be provided other means for retaining the bone drain in the chosen implanted position. There may be a plurality of drain apertures along the length of the drain. The implantable drain may be used in the treatment of bone pain in a range of arthritic and other orthopaedic disorders and may also retard degenerative disease.

6 Claims, 1 Drawing Sheet

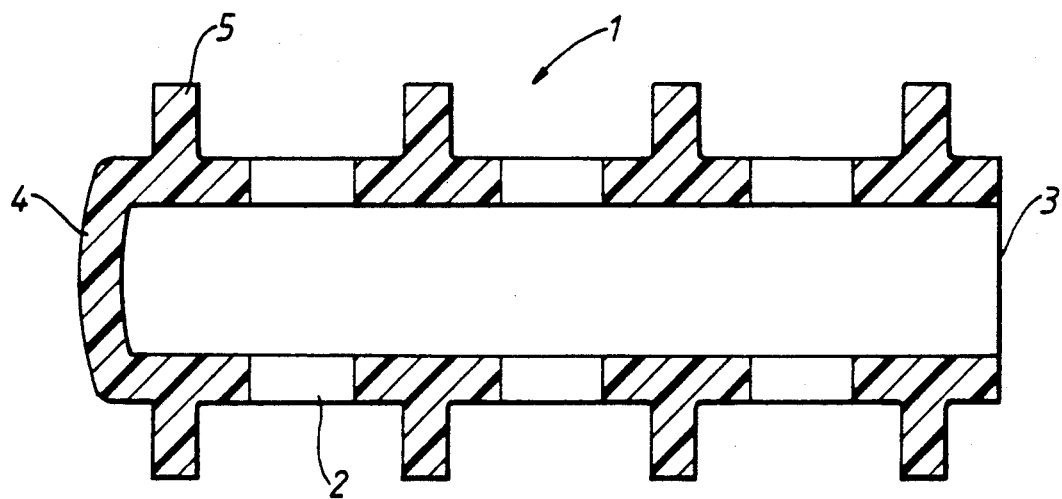

IMPLANTABLE BONE DRAIN

This is a continuation of co-pending application Ser. No. 318,924 filed on Feb. 23, 1989 abandoned.

The present invention is based on the appreciation that long-term relief of intraosseous pressure ("IOP") should prove to be effective in the treatment of a wide range of arthritic and other orthopaedic disorders, for example, aseptic necrosis of bone, bone ischaemias generally and Perthes disease.

The invention provides an implantable bone drain for relieving intraosseous pressure, which is formed of a bio-compatible material and of which the outer surface is so shaped as to prevent or limit movement of the drain out of position after implantation, and/or there is provided other means for retaining the bone drain in the chosen implanted position.

An implantable bone drain according to the invention may be used in the treatment of bone pain in a wide range of bone disorders. Moreover, the resulting relief of IOP improves bone perfusion and tends to retard degenerative disease. In particular, it is considered that early implantation of a bone drain in accordance with the invention may significantly defer the need for joint replacement in certain arthritic conditions.

In use, the bone drain will normally be introduced into sub-chondral cancellous bone with its free end either flush with the bone surface or projecting slightly beyond the bone wall into the surrounding tissue. Alternatively, in the case of a bone drain formed of a sufficiently flexible material, the projecting free end portion may be bent so as to lie along the outer surface of the bone and then secured into a suitable position, for example, by suturing to tissue. As compared with previously proposed bone screws designed for insertion into cortical bone (in the metaphysis), the bone drain of the invention is primarily designed to provide drainage from under cartilege (i.e. from sub-chondral cancellous bone). Accordingly, the bone drain of the invention should be so shaped, constructed and dimensioned that it can be implanted so as to provide drainage from specific sub-chondral sites.

It is essential that the bone drain should remain in the chosen position after implantation, with substantially no "creep", and accordingly its outer surface is preferably so shaped as to prevent or at least limit movement of the implanted drain out of position. To that end, the outer surface of the bone drain is advantageously formed with one or, preferably, a plurality of outwardly extending resiliently flexible or deformable projections. Typically, the or each such projection may extend for from 2 to 3 mm. From the outer surface of the drain. For example, there may be a plurality of radially-extending projections arranged in a star configuration around the drain body, and preferably there is a plurality of such star configurations arranged at intervals along the drain. Alternatively or additionally, there may be one or more circumferentially-extending continuous projections. In general, it is recommended that the or each projection should extend transversely with respect to the drain, and the use of projections which are inclined with respect to the direction of insertion of the drain is generally not advisable although the projections may be arranged to define a screw thread allowing the drain to be screwed into or out of a bone.

In one possible arrangement having a plurality of projections, each successive projection along the length of the drain extends a progressively shorter distance from the drain surface. This configuration tends to facilitate insertion of the drain into the bone.

In addition to or instead of having the outer surface of the drain shaped as described above to prevent or limit movement, there may be provided other means for retaining the bone drain in the chosen implanted position. For example a K wire may be used to hold the drain in position or the drain may be sutured to suitably placed bone or muscle. Preferably, however, the bone drain of the invention is not provided with any enlarged retaining head or collar. A drain having such a head or collar would be difficult or impossible to implant along a direction that is inclined with respect to the bone surface, and this could in turn make it difficult or impossible to gain access to specific sub-chondral sites.

Although a bone drain according to the invention could in principle be formed of a rigid material, it is preferably formed of a material having some flexibility, and preferably a resiliently flexible material. Preferred materials are semi-rigid (as distinct, for example, from materials having the extreme flexibility of soft rubber). In any case, it will normally be essential for any outwardly extending projections to be formed of flexible material, preferably a resiliently flexible material. Preferably, the drain is formed of a biologically inert plastics material such as, for example, ultra high molecular weight polyvinyl chloride (UPVC). Other possible materials are, for example: ultra high molecular weight polyethylene, polytetrafluoroethylene (PTFE, preferably woven), silicone elastomers (for instance that sold under the trade name "SILASTIC"), the material that is sold under the trade name "DACRON" (preferably woven), carbon fibre, carbon fibre reinforced plastics materials, ceramic materials or biocompatible metals or metal alloys. Suitable metals and allows include stainless steel, titanium and titanium/vanadium alloys.

In selecting the material(s) to be used it must of course be borne in mind that it will in many cases be intended that the bone drain should be implanted for a period of years, and the material should advantageously be one that will not crack or otherwise fail even after prolonged implantation.

In general, a bone drain according to the invention will be of a generally tubular form. The external diameter of the tube will depend in part on the nature of the bone site at which it is to be inserted, but (disregarding any projections) will in general be in the range of from 3 to 15 mm.

As an alternative to a drain of generally tubular form, there may, for example, be provided a drain having a solid central portion with one or more fluid passageways defined around the solid portion. Such passageways may be entirely open along their outer sides; thus the bone drain may, for example, have a star shaped cross-section.

Advantageously, a bone drain according to the invention comprises a hollow tubular body having a plurality of drain apertures arranged along its length, and preferably along substantially the whole of its length. Preferably, the drain apertures are arranged substantially uniformly across the surface of the hollow tube.

It is undesirable for the drain apertures to be too small, otherwise there is a risk that they will be blocked by ingrowth after implantation. Advantageously, the size and disposition of the apertures in such that the aggregate area of the apertures is in the range of from 10 to 90%, preferably about 30%, of the total external surface area of the tubular body (disregarding any projections).

The internal diameter of a bone drain according to the invention in the form of a hollow tubular body may be in the range of from 1 to 10 mm. The wall thickness of the hollow tubular body may be in the range of from ½ to 5 mm.

The length of a bone drain according to the invention will depend on the location of the particular sub-chondral site that is to be drained. Typically the length may be at least 5 cm and may be as much as 10 cm. In certain applications, however, the length may be as little as 2 cm or even 1 cm and in other applications the length may be as much as 20 cm.

There may in some cases be advantages in providing a bone drain according to the invention with a non-return valve at the outlet end. When such a valve is fitted, fluctuating IOP will not lead to a temporarily higher pressure beyond the outlet of the drain than in the bone and the possibility of drained fluid returning into the drain in such circumstances is thus eliminated and the inflow of arterial blood to the area drained facilitated.

Both in order to facilitate the initial insertion of the bone drain under x-ray monitoring and to enable its exact position within the bone to be determined at any time after insertion, it is important that the bone drain should be provided with a radio-opaque marker and/or that it be wholly or partly formed of a radio-opaque material. A suitable marker may comprise, for example, a series of spots of a radio-opaque coating material (for example, a lead or barium-based paint) spaced apart along the drain, but preferably comprises a radio-opaque continuous rectilinear band or spiral which extends along the whole length of the drain.

To prepare the bone for insertion of the drain, a hole of diameter approximately 1 mm less than the overall diameter of the drain (including any projections) is made in the bone wall at the selected site, and is drilled or reamed out to form a bore of the desired length. For this purpose there may be used sheathed reamers which fit over standard guide wires for so-called "closed" insertion under x-ray control.

In order to facilitate the insertion of a drain which comprises a hollow tubular body, one end of the body may be closed. It is then possible to push the drain into position using a trochar or other suitable instrument which is withdrawn once the desired position has been reached.

Advantageously, to minimise the risk of infection, a bone drain according to the invention is formed of an antibiotic loaded material from which the antibiotic diffuses out gradually after implantation. Alternatively spaces formed in the drain may be packed with an antibiotic.

In principle, a bone drain according to the invention should be so constructed that it can be removed without an "open" surgical operation. Removal will normally be carried out with x-ray monitoring. The tensile strength of the material used to make the drain should be such that it can be pulsed out of its implanted position without rupturing. In order to increase the tensile strength of the bone drain, a strengthening fibre may be woven into the drain as an integral part thereof.

In the case of a hollow tubular perforated drain, removal may be effected by engaging a perforation by means of a hook-shaped probe. Alternatively, the drain may be formed with one or more loops or projections in its interior, and such loops or projections can be engaged by a hook-shaped probe or similar instrument when it is desired to remove it.

Other methods of insertion or removal may be employed. For example, the drain may be constructed so as to be of variable diameter and may be inserted and removed while at a smaller diameter than that which it has while installed in the bone. The change in diameter of the drain may be achieved by the application of traction along its longitudinal axis.

In the case of a bone drain comprising a hollow tubular body having apertures along its length, there is self-evidently a channel available for relieving intraosseous pressure and, to a certain extent, allowing drainage of blood. There may to a certain extent be growth of fibrous material within the channel after implantation for a prolonged period, but such fibrous material will itself be sufficiently fluid-permeable to allow the pressure relief and drainage process to operate. In addition, there will not be a perfect interlock between the outer surface of the drain and the surrounding bone, and that boundary zone will also become filled with similar fluid-permeable fibrous material. That will provide an additional drainage and pressure relief pathway in a hollow perforated bone drain and will constitute the sole pathway in a solid drain.

In the case of an open-ended hollow tubular drain, it may conveniently be supplied as continuous tubing which is cut to the desired length at the time of implantation. A solid drain may be supplied in a similar way. In the case of tubes having closed ends, these may be supplied in individual sections which may be cut to the desired length.

A single bone drain according to the invention may be used alone or a plurality of bone drains may be implanted in a bone at adjacent sites. In the case where a plurality of drains are implanted these may be led along a common path to the bone.

One form of bone drain according to the invention will now be described, by way of example, with reference to the accompanying drawing, which shows the drain in longitudinal section.

The drain shown in the drawing of FIG. 1 comprises a hollow tubular body which is indicated generally by the reference numeral 1 and is formed of a suitable bio-compatible, flexible plastics material. The tubular body is formed with a plurality of apertures 2 along its length. The free end 3 of the tubular body is open, whilst the other end 4 is closed.

The tubular body 1 is formed with a plurality of outwardly extending flexible and/or deformable projections 5, arranged in star-shaped configurations around the circumference of the tube.

The dimensions of the bone drain shown in the drawing may be for example, as follows:

| Internal diameter | 5 mm |
| Wall thickness | 1-2 mm |
| Length of each projection | 2-3 mm |

It is important to note that the bone drain of the invention is designed to provide relief of pressure rather than to drain substantial volumes of fluid. Typically, the total fluid drainage through a bone drain according to the invention will be approximately 2 ml. per day.

I claim:

1. A process of relieving intraosseous pressure in sub-chondral cancellous bone tissue, which comprises:

forming a bore hole in the tissue; and inserting a tubular body into the bore hole, said body being formed of a biocompatible material and having (i) a channel communicating between the body and the body exterior;

(ii) integral means for fixing the body in the bore hole; and (iii) a plurality of drain apertures arranged along its length.

2. The process of claim 1 wherein the drain apertures are arranged along substantially the whole of the length of the tubular body.

3. The process of claim 2 wherein the size and disposition of the apertures is such that the aggregate area of the apertures is in the range of from 10 to 90 percent, of the total external surface area of the tubular body.

4. The process of claim 1 wherein the internal diameter of the tubular body is in the range of from 1 to 10 millimeters.

5. The process of claim 1 wherein the wall thickness of the tubular body is in the range of from 0.5 to 5 millimeters.

6. The process of claim 1 wherein one end of the body is closed.

* * * * *